United States Patent [19]

Umezawa et al.

[11] Patent Number: 4,576,931

[45] Date of Patent: Mar. 18, 1986

[54] 23-C-SUBSTITUTED MYCAMINOSYL TYLONOLIDE, PHARMACEUTICAL COMPOSITIONS AND METHOD OF USE

[75] Inventors: Hamao Umezawa; Sumio Umezawa, both of Tokyo; Tsutomu Tsuchiya, Kanagawa; Tomio Takeuchi, Tokyo; Akihiro Tanaka, Tokyo; Shuichi Sakamoto, Tokyo, all of Japan

[73] Assignee: Zaidan Hojin Biseibutsu Kagaku Kenkyu Kai (Microbial Chemistry Research Foundation), Tokyo, Japan

[21] Appl. No.: 719,286

[22] Filed: Apr. 3, 1985

[51] Int. Cl.⁴ .................. A61K 31/78; C07H 17/08
[52] U.S. Cl. ........................... 514/30; 536/7.1
[58] Field of Search ..................... 536/7.1; 514/30

[56] References Cited

U.S. PATENT DOCUMENTS 4,056,616 11/1977 Reimann et al. .................. 536/7.1
4,401,660 8/1983 Kirst ................................. 536/7.1

OTHER PUBLICATIONS

Pigman et al., "Chemistry of the Carbohydrates", 1948, Academic Press Inc., New York, N.Y.

Primary Examiner—Johnnie R. Brown
Attorney, Agent, or Firm—Burgess, Ryan & Wayne

[57] ABSTRACT

Novel 23-C-substituted mycaminosyl tylonolide of the general formula (I)

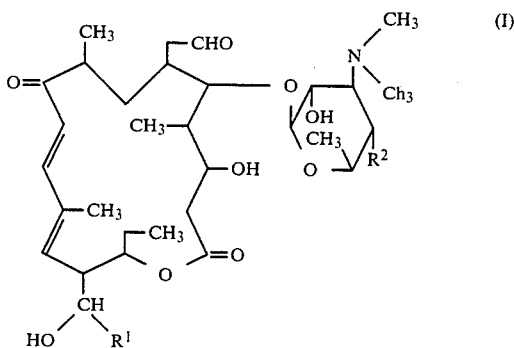

wherein $R^1$ represents a lower alkyl group, an aryl group, a lower alkenyl group or a lower alkynyl group, $R^2$ represents a hydrogen atom or a hydroxyl group.

These compounds have excellent antibacterial activities.

13 Claims, No Drawings

23-C-SUBSTITUTED MYCAMINOSYL TYLONOLIDE, PHARMACEUTICAL COMPOSITIONS AND METHOD OF USE

BACKGROUND OF THE INVENTION AND THE PRIOR ART

British Patent Publication No. 2,081,711 or Unexamined European Patent Publication No. 70,170 discloses tylosin compounds having only mycaminose or desosamine as sugar component. These publications disclose tylosin compounds wherein the 23-position carbon atom has a substituent such as a halogen atom, a hydroxyl group, an alkanoyloxy group,

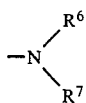

(wherein $R^6$ represents a hydrogen atom or a lower alkyl group which may be substituted by a hydroxyl group, $R^7$ represents a hydrogen atom, an alkyl group which may be substituted by a hydroxyl group, an aryl group, an aralkyl group, etc.), etc.

The compounds of this invention of the formula (I) are novel compounds having excellent antibacterial activity, and have a characteristic in that the 23-position carbon atom has a substituent selected from a lower alkyl group, an aryl group, a lower alkenyl group, or a lower alkynyl group.

DETAILED DESCRIPTION OF THE INVENTION

This invention relates to antibacterial compounds which show antibacterial activity against various pathogens including gram-positive and -negative bacteria, the production of these compounds, and medical compositions containing them.

The compounds of this invention are those of the general formula (I)

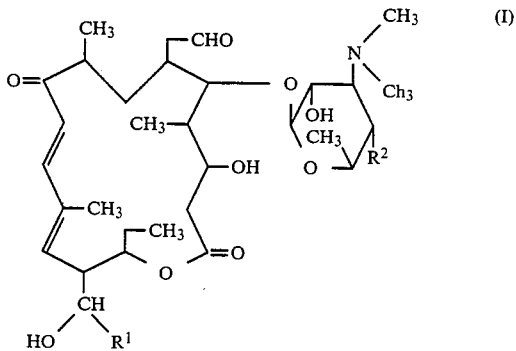

wherein $R^1$ represents a lower alkyl group, an aryl group, a lower alkenyl group or a lower alkinyl group, $R^2$ represents a hydrogen atom or a hydroxyl group.

Symbols herein have the same significances throughout unless otherwise indicated.

The term "lower alkyl" in the foregoing definitions means a straight or branched carbon chain alkyl having 1 to 5 carbom atoms. Thus, examples of the "lower alkyl" are methyl, ethyl, n-propyl, iso-propyl, n-butyl, iso-butyl, sec-butyl and tert-butyl. Examples of the "aryl" in the foregoing definitions are phenyl, naphthyl, etc. The term "lower alkenyl" in the foregoing definitions means a straight or branched carbon chain alkenyl having 2 to 6 carbon atoms and having one or two double bonds. Thus examples of the "lower alkenyl" are vinyl ($CH_2=CH-$), 1-propenyl ($CH_3-CH=CH-$), 2-propenyl ($CH_2=CH-CH_2-$), iso-propenyl

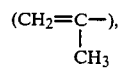

2-butenyl ($CH_3-CH=CH-CH_2-$), 2-pentenyl ($CH_3-CH_2-CH=CH-CH_2-$), etc. The term "lower alkynyl" in the foregoing definitions means a straight or branched carbon chain alkinyl having 2 to 6 carbon atoms and having triple bond(s). Thus examples of the "lower alkynyl" are ethynyl ($CH\equiv C-$), 2-propargyl ($CH\equiv C-CH_2-$), 2-butinyl ($CH_3-C\equiv C-CH_2-$), 2-penten-4-ynyl ($CH\equiv C-CH=CH-CH_2$), etc.

The compounds of this invention have an asymmetric carbon atom at the 23-position, and so, there are optical isomers. Thus this invention includes all of the isomers, individually and in any combination, e.g. racemic compound(s), optically active isomer(s), etc.

The compounds of this invention have shown antibacterial activity against various pathogens including gram-positive and -negative bacteria, and, in particular, the compounds have shown the activity against several important gram-negative bacteria. Thus, the compounds are useful for medicaments (especially, antibiotics) for the prevention or treatment of diseases caused by such bacteria.

Antibacterial medicaments containing the compounds according to this invention can be prepared by by conventional methods using conventional carriers or excipients; such carriers or excipients may be organic or inorganic, solid or liquid materials which are pharmaceutically acceptable and suitable for oral or parenteral administration or for external application. They may for example be administered as capsules, tablets (such as sugar-coated tablets), ointments, suppositories, solutions, suspensions, emulsions, etc. The appropriate dose is determined in each case considering factors such as the symptom, age and sex of the patient, but for an adult 10-1000 mg per single dose is usually administered in one to four doses per day.

Concerning the antimicrobial activity of the compounds of this invention of the formula (I), minimum effective inhibitory concentrations (MIC) of the compounds are shown in the following Table.

TABLE

| | (MIC γ/ml) MT:mycaminosyl tylonolide DT: 4' deoxy mycaminosyl/tylonolide | | | | | | | | | | |
|---|---|---|---|---|---|---|---|---|---|---|---|
| | Control | | Example No. | | | | | | | | |
| Strain | MT | DT | 1(3) | 2(2) | 4(2) | 5(2) | 6 | 8 "F" | 10 "F" | 11 "F" | 12 "F" |
| B. Subtilis NRRL B-558 | 3.12 | 1.56 | 0.78 | 0.78 | 0.39 | 0.39 | 0.39 | 0.39 | 0.39 | 3.12 | 0.78 |
| M. luteus PCI 1001 | <0.2 | <0.2 | <0.2 | <0.2 | <0.2 | <0.2 | <0.2 | <0.2 | <0.2 | <0.2 | <0.2 |

TABLE-continued (MIC γ/ml) MT:mycaminosyl tylonolide DT: 4' deoxy mycaminosyl/tylonolide

| Strain | Control | | Example No. | | | | | | | | |
|---|---|---|---|---|---|---|---|---|---|---|---|
| | MT | DT | 1(3) | 2(2) | 4(2) | 5(2) | 6 | 8 "F" | 10 "F" | 11 "F" | 12 "F" |
| Staph. aureus Smith | 1.56 | 0.39 | 1.56 | 1.56 | 0.78 | 0.39 | 0.39 | <0.2 | 0.78 | 1.56 | 0.78 |
| Kl. pnuemoniae PCI-602 | 3.12 | 1.56 | 3.12 | 3.12 | 6.25 | 1.56 | 3.12 | 3.12 | 3.12 | 3.12 | 1.56 |
| Sal. entiritidis 1981 | 3.12 | 1.56 | 3.12 | 3.12 | 3.12 | 3.12 | 3.12 | 3.12 | 3.12 | 3.12 | 3.12 |
| Psued. aeruginosa A3 | 25 | 12.5 | 12.5 | 12.5 | 6.25 | 25 | 12.5 | 6.25 | — | 6.25 | 3.12 |

The compounds of this invention can be produced by the following procedure:

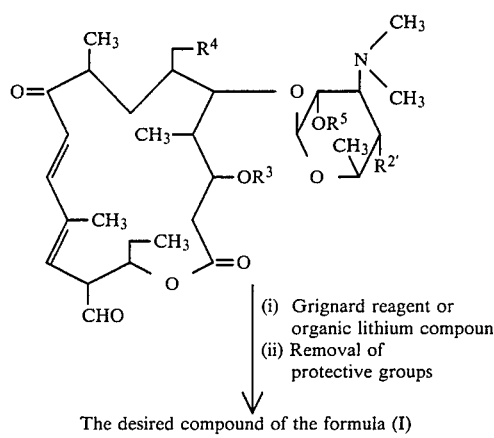

The desired compound of the formula (I)

In the above formulas, $R^{2'}$ represents a hydrogen atom or a protected hydroxyl group, $R^3$ represents a protective group for a hydroxyl group, $R^4$ represents a protected aldehyde group, $R^5$ represents a protective group for a hydroxyl group.

The compounds (I) can thus be produced by reacting 23-deoxy-23-oxo-mycaminosyl tylonolide derivatives of formula (II) with Grignard reagent of the formula: $R^1MgX$ (wherein $R^1$ is as defined above, and X represents a halogen atom) or with organic lithium compound of the formula: $R^1$-Li (wherein $R^1$ is as defined above) [step 1], and then releasing protective groups for hydroxyl groups and aldehyde-protective group [step 2].

Practical examples of the protective group for hydroxyl groups are as follows:

Protective group for a hydroxy group in the case of $R^{2'}$ and $R^5$: a lower acyl group such as an acetyl group, a propionyl group, a butyryl group, etc.

Protective group for a hydroxyl group in the case of $R^3$: a tert-butyldimethylsilyl group, a 2-pyranyl group, a 2-furanyl group, etc.

Protected aldehyde in the case of $R^4$: acetal or thioacetal; practically, dimethylacetal, diethylacetal, diethylthioacetal, ethyleneacetal, ethylenethioacetal, propyleneacetal, etc.

Examples of Grignard reagent of the formula: $R^1MgX$ are lower alkyl magnesium halide (such as methyl magnesium bromide, ethyl magnesium bromide, butyl magnesium bromide, etc.), aryl magnesium halide (such as phenyl magnesium bromide, naphthyl magnesium bromide, etc.), lower alkenyl magnesium halide (such as, vinyl magnesium bromide, 2-propenyl magnesium bromide, etc.) and lower alkinyl magnesium halide (such as ethinyl magnesium bromide, 2-propynyl magnesium bromide), etc. And examples of the organic lithium compound of the formula: $R^1$-Li are methyl lithium ($CH_3Li$), butyl lithium ($CH_3$—$CH_2$—$CH_2$—$CH_2Li$), ethylene lithium ($CH_2$=$CHLi$), 2-propene lithium, 2-propine lithium, 2-phenyl lithium, etc.

The reaction of the starting material (II) with the Grignard reagent or the organic lithium compound [step 1] is usually performed in an organic solvent (such as dry ether, tetrahydrofuran, etc.) at low temperature (for example, $-50°$ to $-80°$ C.). The reaction can be completed within 1 to 3 hours.

The compounds thus formed are usually racemic compounds. If optical active isomers are desired, the formed products are subjected to a conventional manner such as silica gel column chromatography to isolate each of the optical isomers.

The compounds (I) can be obtained after releasing the protective groups [step 2]. The removal of $R^{2'}$ and $R^5$ (protective groups for 2'- and 4'-hydroxyl groups of mycaminose) is easily performed in a conventional manner for example, by heating in a suitable solvent such as methanol, a water-containing alcohol, an aprotic solvent containing water. The removal of $R^3$ (protective group for hydroxyl group) and the aldehyde protective group can be performed in a conventional manner, for example, by treatment with mineral acid such as hydrochloric acid, sulfuric acid, etc. or organic acid such as trifluoroacetic acid, trichloroacetic acid, etc.

The invention is illustrated by the following Examples. The production methods for some of the starting materials for this invention are shown by the following Reference Examples. In these Examples NMR means a nuclear magnetic resonance spectrum, and Me means a methyl group; the quoted chromatography eluant ratios are by volume.

REFERENCE EXAMPLE 1

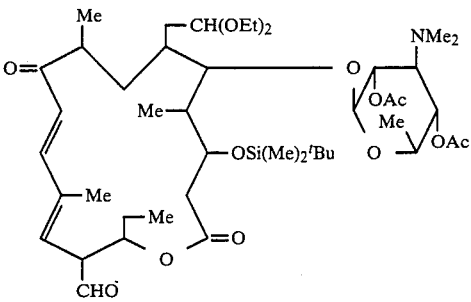

673 mg of 2',4'-di-O-acetyl-3-O-tert-butyldimethylsilyl mycaminosyl tylonolide diethylacetal was dissolved in 6.6 ml of dry benzene and 6.6 ml of dry dimethyl sulfoxide. After adding thereto 150 mg of pyridinium trifluoroacetate and 624 mg of N,N'-dicyclohexyl carbodiimide, the mixture was stirred at room temperature for 5 hours. The reaction mixture was added to a solution of 255 mg of oxalic acid dihydrate in 6.6 ml of dioxane, and the mixture was stirred for 1 hour at room temperature. The precipitates thus formed were removed by filtration and the reaction solution was concentrated under reduce pressure to give a syrupy material. The syrupy material was dissolved in 100 ml of benzene. The solution was washed with saturated aqueous sodium hydrogen carbonate, saturated aqueous sodium sulfate, and dried over anhydrous sodium sulfate. The solution was concentrated under reduced pressure to give 700 mg of a solid material of 2',4'-di-O-acetyl-3-O-tert-butyldimethylsilyl-23-deoxy-23-oxo-mycaminosyl tylonolide diethylacetal. This product was used for the next reaction step, without purification.

REFERENCE EXAMPLE 2

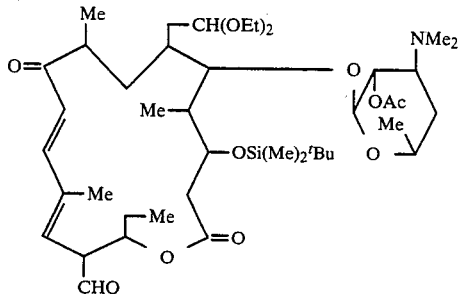

900 mg of 2'-O-acetyl-3-O-tert-butyldimethylsilyl-4'-deoxymycaminosyl tylonolide diethyl acetal was dissolved in 9 ml of dry benzene and 9 ml of dry dimethyl sulfoxide, and after adding thereto 215 mg of pyridinium trifluoroacetate and 914 mg of N,N'-dicyclohexyl carbodiimide, the mixture was stirred at room temperature for 4 hours. The reaction mixture was poured into a solution of 372 mg of oxalic acid dihydrate in 9 ml of dioxane, and the mixture was stirred for 1 hour. Insoluble materials were removed by filtration, and the filtrate was concentrated under reduced pressure. A syrupy material obtained was dissolved in 100 ml of benzene, and the solution was washed with saturated aqueous sodium hydrogencarbonate, saturated aqueous sodium sulfate, dried over anhydrous sodium sulfate, and concentrated under reduced pressure to give 1 g of a solid material of 2'-O-acetyl-3-O-tert-butyldimethylsilyl-23,4'-dideoxy-23-oxo-mycaminosyl tylonolide diethylacetal. This product was used for the next reaction step, without purification.

EXAMPLE 1

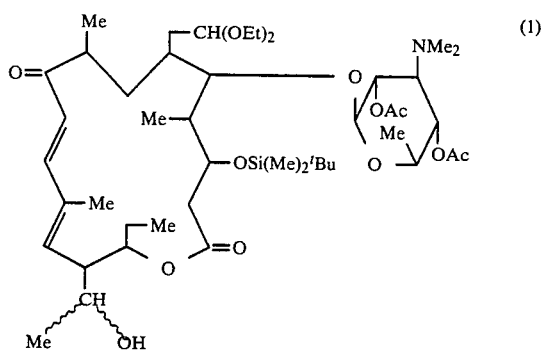

To a cold solution (−78° C.) of 0.67 g of 2',4'-O-acetyl-3-O-tert-butyldimetylsilyl-23-deoxy-23-oxo-mycaminosyl tylonolide diethylacetal in 7 ml of dry tetrahydrofuran, was added 1 ml of 1M tetrahydrofuran solution of methyl magnesium bromide. It was kept for 3 hours at that temperature.

The reaction mixture was poured into saturated aqueous ammonium chloride, and extracted with 35 ml of chloroform. The extract was washed with saturated aqueous sodium sulfate, dried over anhydrous sodium sulfate, and concentrated under reduced pressure.

The residue was chromatographed (Kiesel gel-60: 70 g; toluene:ethyl acetate: 5:2-1:1) to give 230 mg of one optical isomer (A) and 180 mg of another optical isomer (B) of 2',4'-di-O-acetyl-3-O-tert-butyldimethylsilyl-23-C-methylmycaminosyl tylonolide diethylacetal (these optical isomers are those caused by the 23-position asymmetric carbon atom).

| NMR (CDCl$_3$) | | | |
|---|---|---|---|
| (A) | δ (ppm) | | |
| | 0.83 | 9H | 3-O—Si(Me)$_2$—$^t$Bu |
| | 1.12 | 3H | 23-C—Me |
| | 2.07 | 6H | 2',4'-OCOCH$_3$ |
| | 2.35 | 6H | N—Me$_2$ |
| | 4.10 | 1H | 23-CH(OH)(Me) |
| (B) | δ (ppm) | | |
| | 0.88 | 9H | 3-O—Si(Me)$_2$—$^t$Bu |
| | 1.21 | 3H | 23-C—Me |
| | 2.08 | 6H | 2',4'-OCOCH$_3$ |
| | 2.36 | 6H | N—Me$_2$ |
| | 3.99 | 1H | 23-CH(OH)(Me) |

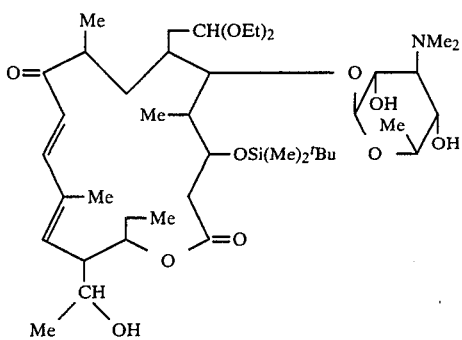
(2)

A solution of 230 mg of the optical isomer (A) of 2′,4′-di-O-acetyl-3-O-tert-butyldimethylsilyl-23-C-methylmycaminosyl tylonolide diethylacetal in 5 ml of methanol was kept at 50° C. overnight. The reaction mixture was concentrated under reduced pressure to give 200 mg of 3-O-tert-butyldimethylsilyl-23-C-methylmycaminosyl tylonolide diethylacetal.

| NMR (CDCl₃) | | |
|---|---|---|
| δ (ppm) | | |
| 0.88 | 9H | 3-O—Si(Me)₂ $^tBu$ |
| 2.55 | 6H | N—Me₂ |
| 4.70 | 1H | H-23 |
| 6.07 | 1H | H-13 |

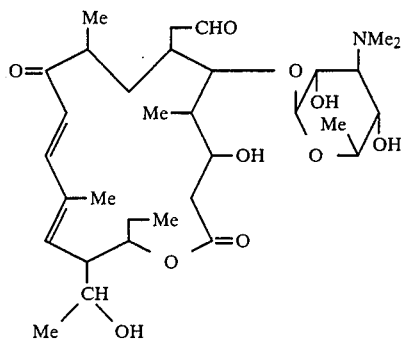
(3)

A solution of 200 mg of 3-O-tert-butyldimethylsilyl-23-C-methylmycaminosyl tylonolide diethylacetal (obtained at (2) above) in 1.2 ml of acetonitrile and 1.2 ml of 1N hydrochloric acid was kept at room temperature overnight. To the reaction mixture was added saturated aqueous sodium hydrogencarbonate (pH 9), and the mixture was extracted with 3 ml of chloroform, which was washed with 3 ml of a saturated aqueous sodium sulfate solution, dried over anhydrous sodium sulfate, and concentrated under reduced pressure. The residue was chromatographed (Kiesel gel-60: 18 g; chloroform:methanol: 28% aqueous ammonia: 10:1:0.1) to give 121 mg of 23-C-methylmycaminosyl tylonolide.

| NMR (CDCl₃) | | |
|---|---|---|
| δ (ppm) | | |
| 1.15 | 3H | 23-C—Me |
| 1.81 | 3H | 22-Me |
| 2.51 | 6H | N—Me₂ |
| 4.08 | 1H | H-23 |
| 4.26 | 1H | H-1′ |
| 5.20 | 1H | H-15 |

-continued

| NMR (CDCl₃) | | |
|---|---|---|
| 6.07 | 1H | H-13 |
| 9.69 | 1H | H-20 |

EXAMPLE 2

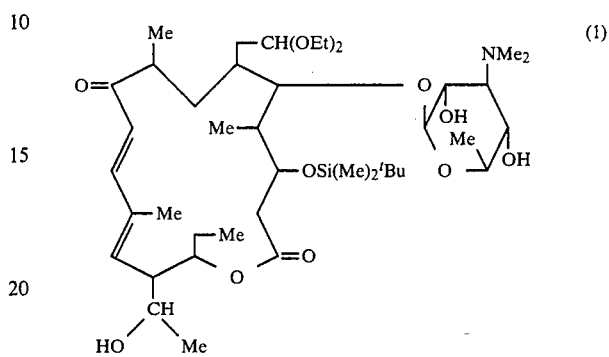
(1)

A solution of 114 mg of the optical isomer (B) obtained by Example 1 (1) of 2′,4′-di-O-acetyl-3-O-tert-butyldimethylsilyl-23-C-methylmycaminosyl tylonolide diethylacetal in 2.2 ml of methanol was kept at 50° C. overnight.

It was concentrated under reduced pressure, and the residue was chromatographed (Kiesel gel-60: 22 g; chloroform:methanol: 12:1-5:1) to give 70 mg of 3-O-tert-butyldimethylsilyl-23-C-methylmycaminosyl tylonolide diethylacetal.

| NMR (CDCl₃) | | |
|---|---|---|
| δ (ppm) | | |
| 0.88 | 9H | 3-O—Si(Me)₂ $^tBu$ |
| 2.55 | 6H | N—Me₂ |
| 4.01 | 1H | H-23 |
| 5.80 | 1H | H-13 |

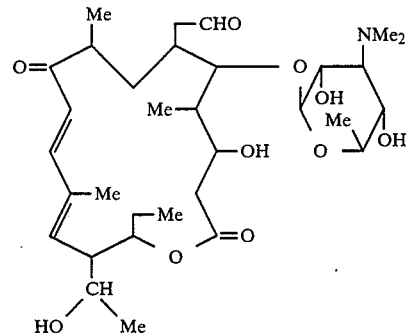
(2)

A solution of 53 mg of 3-O-tert-butyldimethylsilyl-23-C-methylmycaminosyl tylonolide diethylacetal (obtained at (1) above) in 0.27 ml of acetonitrile and 0.27 ml of 1N hydrochloric acid was kept at room temperature overnight Usual work-up (cf. Ex.1(3)) gave a solid, which was chromatographed (Kiesel gel-60: chloroform:methanol: 28% aqueous ammonia solution: 10:1:0.1) to give 22 mg of 23-C-methylmycaminosyl tylonolide diethylacetal.

| NMR (CDCl₃) | | |
|---|---|---|
| δ (ppm) | | |
| 1.23 | 3H | 23-C—Me |
| 1.83 | 3H | 22-Me |
| 2.50 | 6H | N—Me₂ |
| 3.98 | 1H | H-23 |
| 4.28 | 1H | H-1' |
| 4.91 | 1H | H-15 |
| 5.76 | 1H | H-13 |
| 9.70 | 1H | H-20 |

EXAMPLE 3

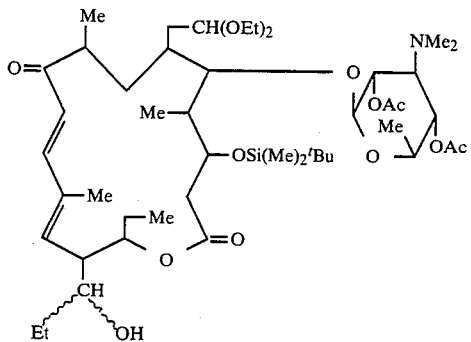

(1)

To a solution of 1.01 g of 2',4'-di-O-acetyl-3-O-tert-butyldimethylsilyl-23-deoxy-23-oxo-mycaminosyl tylonolide diethylacetal in 10.5 ml of dry tetrahydrofuran, was added 0.89 ml of 3M diethyl ether solution of ethyl magnesium bromide at −78° C. After 1 hour, the reaction mixture was poured into a saturated aqueous ammonium chloride solution. Usual workup (cf. Ex.1(1)) gave a solid, which was chromatographed (Kiesel gel-60: 50 g; toluene:ethyl acetate: 3:1) to give 397.7 mg of one optical isomer (A) and 312.5 mg of another optical isomer (B) of 2',4'-di-O-acetyl-3-O-tert-butyldimethylsilyl-23-C-ethylmycaminosyl tylonolide diethylacetal (these optical isomers are those caused by the 23-position asymmetric carbon atom).

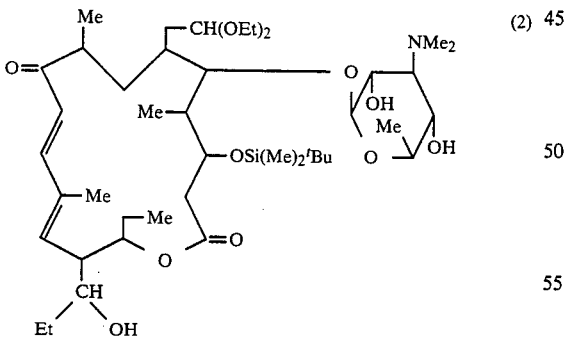

(2)

A solution of 397.7 mg of the optical isomer (A) obtained at (1) above of 2',4'-di-O-acetyl-3-O-tert-butyldimethylsilyl-23-C-ethylmycaminosyl tylonolide diethylacetal in 12 ml of methanol was kept at 50° C. overnight.

Usual work-up gave a solid, which was chromatographed (Kiesel gel-60: 50 g; chloroform:methanol: 28% aqueous ammonia solution: 15:1:0.1) to give 271.3 mg of 3-O-tert-butyldimethylsilyl-23-C-ethylmycaminosyl tylonolide diethylacetal.

| NMR (CDCl₃) | | |
|---|---|---|
| δ (ppm) | | |
| 0.87 | 9H | 3-O—Si(Me)₂ ᵗBu |
| 2.56 | 6H | NMe₂ |
| 4.06 | 1H | H-23 |
| 6.00 | 1H | H-13 |

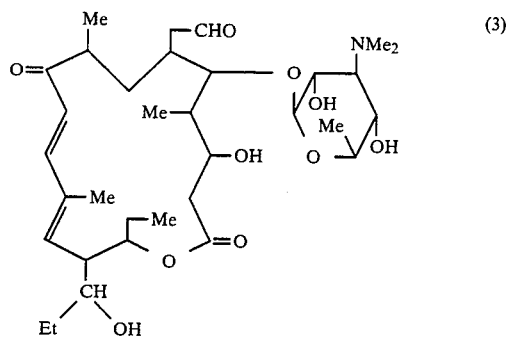

(3)

A solution of 60 mg of 3-O-tert-butyldimethylsilyl-23-C-ethylmycaminosyl tylonolide diethylacetal (obtained at (2) above) in 0.3 ml of acetonitrile and 0.3 ml of 1N hydrochloric acid was kept at 37° C. overnight. Usual work-up (cf. Ex.1(3)) gave a solid which was chromatographed (Kiesl gel-60: 6 g, chloroform:methanol: 28% aqueous ammonia solution: 20:1:0.1–15:1:0.1) to give 33.7 mg of 23-C-ethylmycaminosyl tylonolide.

| NMR (CDCl₃) | | |
|---|---|---|
| δ (ppm) | | |
| 0.90 | 3H | 23-CH₂CH₃ |
| 1.42 | 2H | 23-CH₂CH₃ |
| 1.81 | 3H | 22-Me |
| 2.52 | 6H | NMe₂ |
| 4.27 | 1H | H-1' |
| 5.24 | 1H | H-15 |
| 6.06 | 1H | H-13 |
| 9.68 | 1H | H-20 |

EXAMPLE 4

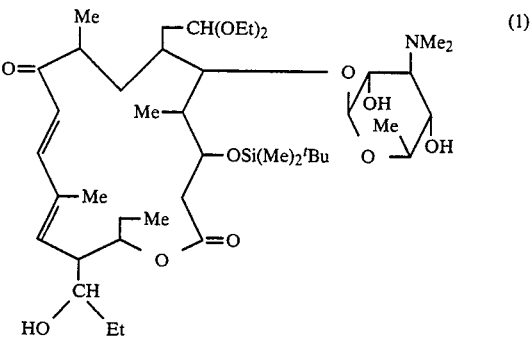

(1)

A solution of 312.5 mg of the optical isomer (B) obtained by Example 3 (1) of 2',4'-di-O-acetyl-3-O-tert-butyldimethylsilyl-23-C-ethylmycaminosyl tylonolide diethylacetal in 6.3 ml of methanol was kept at 50° C. overnight. Usual work-up gave a solid, graphed (Kiesel gel-60: 30 g; chloroform:methanol: 28% aqueous ammonia solution: 18:1:0.1) to give 73.2 mg of 3-O-tert-butyldimethylsilyl-23-C-ethylmycaminosyltylonolide diethylacetal.

| NMR (CDCl₃) | | |
|---|---|---|
| δ (ppm) | | |
| 0.87 | 9H | 3-O—Si(Me)₂ ᵗBu |
| 2.56 | 6H | NMe₂ |
| 4.10 | 1H | H-23 |
| 5.75 | 1H | H-13 |

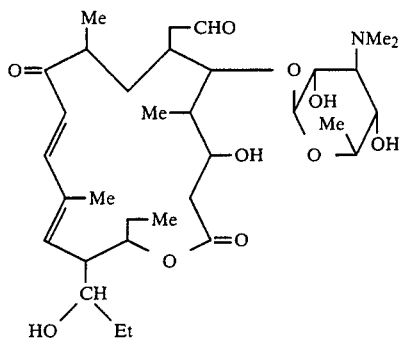
(2)

A solution of 46.4 mg of 3-O-tert-butyldimethylsilyl-23-C-ethylmycaminosyl tylonolide diethylacetal obtained at (1) above in 0.2 ml of acetonitrile and 0.2 ml of 1N hydrochloric acid was kept at room temperature for two days. Usual work-up (cf. Ex.2(2)) gave a solid, which was chromatographed(Kiesel gel-60: 6 g; chloroform:methanol: 28% aqueous ammonia: 20:1:0.1–15:1:0.1) to provide 8.8 mg of 23-C-ethylmycaminosyl tylonolide.

| NMR (CDCl₃) | | |
|---|---|---|
| δ (ppm) | | |
| 0.99 | 3H | 23-C—CH₂CH₃ |
| 1.60 | 2H | 23-C—CH₂CH₃ |
| 1.81 | 3H | 22-Me |
| 2.51 | 6H | NMe₂ |
| 4.27 | 1H | H-1' |
| 4.95 | 1H | H-15 |
| 5.76 | 1H | H-13 |
| 9.70 | 1H | H-20 |

EXAMPLE 5

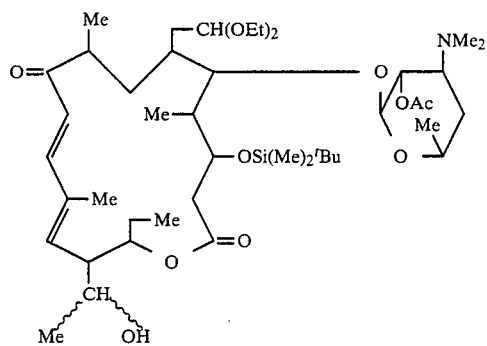
(1)

To a cold (−78° C.) solution of 1 g of 2'-O-acetyl-3-O-tert-butyldimethylsilyl-23-,4'-dideoxy-23-oxo-mycaminosyltylonolide diethylacetal in dry tetrahydrofuran, was added 1.6 ml of 1M tetrahydrofuran solution of methyl magnesium bromide.

After 1 hour, the reaction mixture was poured into saturated aqueous ammonium chloride. Usual work-up (cf. Ex.1(1)) gave a solid, which was chromatographed (Kiesel gel-60: 90 g; toluene:acetone: 4:1–1:1) to give 380 mg of one optical isomer (A) and 160 mg of another optical isomer (B) of 2'-O-acetyl-3-O-tert-butyldimethylsilyl-4'-deoxy-23-C-methylmycaminosyl tylonolide diethylacetal (these isomers are those caused by the 23-position asymmetric carbon).

| NMR (CDCl₃) | | |
|---|---|---|
| (A) δ (ppm) | | |
| 0.86 | 9H | 3-O—Si(Me)₂ ᵗBu |
| 1.12 | 3H | 23-C—Me |
| 2.10 | 3H | 2'-OCOCH₃ |
| 2.27 | 6H | NMe₂ |
| 4.10 | 1H | H-23 |
| 5.97 | 1H | H-13 |
| (B) δ (ppm) | | |
| 0.85 | 9H | 3-O—Si(Me)₂ ᵗBu |
| 1.19 | 3H | 23 C—Me |
| 2.09 | 3H | 2'-OCOCH₃ |
| 2.27 | 6H | NMe₂ |
| 3.98 | 1H | H-23 |
| 5.75 | 1H | H-13 |

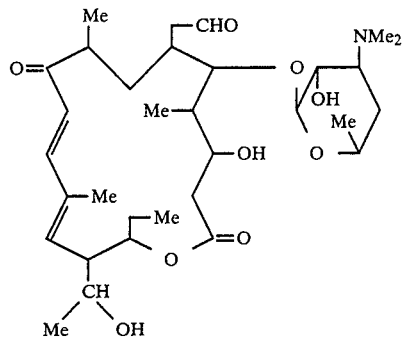
(2)

380 mg of the optical isomer (A) obtained at (1) above of 2'-O-acetyl-3-O-tert-butyldimethylsilyl-4'-deoxy-23-C-methylmycaminosyl tylonolide diethylacetal was subjected to methanolysis and hydrolysis as described before to give a solid, which was chromatographed(Kisel gel-60: 10 g; chloroform:methanol: 28% aqueous ammonia: 15:1:0.1) to provide 130 mg of 4'-deoxy-23-C-methylmycaminosyl tylonolide.

| NMR (CDCl₃) | | |
|---|---|---|
| δ (ppm) | | |
| 1.83 | 3H | 22-Me |
| 2.27 | 6H | NMe₂ |
| 4.22 | 1H | H-1' |
| 9.69 | 1H | CHO |

EXAMPLE 6

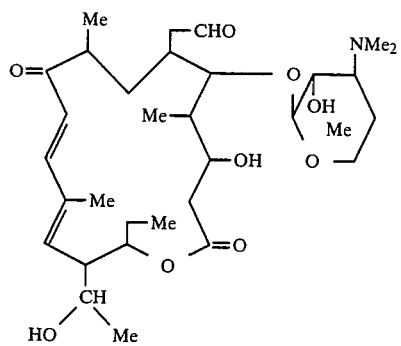

72 mg of the optical isomer (B) obtained by Example 5 (1) of 2'-O-acetyl-3-O-tert-butyldimethylsilyl-4'-deoxy-23-C-methylmycaminosyl tylonolide diethylacetal was treated as described for Example 5(2) to give a solid, which was chromatographed(Kiesel gel-60: 14 g; chloroform:methanol: 20% aqueous ammonia: 15:1:0.1) to provide 26 mg of 4'-deoxy-23-C-methymycaminosyl tylonolide.

| NMR (CDCl$_3$) | | |
|---|---|---|
| δ (ppm) | | |
| 1.24 | 3H | 23-C—Me |
| 1.83 | 3H | 22-Me |
| 2.28 | 6H | NMe$_2$ |
| 3.99 | 1H | H-23 |
| 4.22 | 1H | H-1' |
| 4.89 | 1H | H-15 |
| 5.80 | 1H | H-13 |
| 9.71 | 1H | H-20 |

EXAMPLE 7

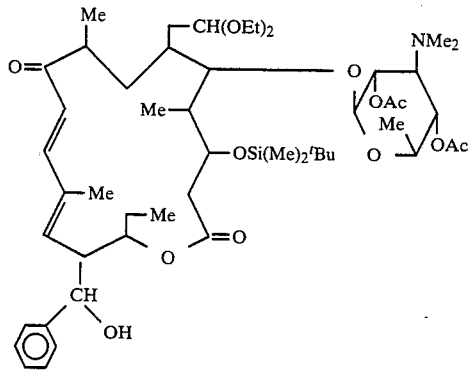
(1)

To a cold (−78° C.) solution of 1 g of 2',4'-di-O-acetyl-3-O-tert-butyldimethylsilyl-23-deoxy-23-oxo-mycaminosyl tylonolide diethyl acetal in 10 ml of tetrahydrofuran, was added 1.2 ml of 2M tetrahydrofuran solution of phenyl magnesium bromide, and it was kept at that temperature for 30 minutes. Usual work-up as described in Ex. 1(1) gave a solid, which was chromatographed(Kiesel gel-60: 50 g; toluene:ethyl acetate: 4:1) to give 587 mg of 2',4'-di-O-acetyl-3-O-tert-butyldimethylsilyl-23-C-phenylmycaminosyl tylonolide diethylacetal.

| NMR (CDCl$_3$) | | |
|---|---|---|
| δ (ppm) | | |
| 0.9 | 9H | 3-O—Si(Me)$_2$$^t$Bu |
| 2.1 | 6H | 2',4'-OCOCH$_3$ |
| 2.35 | 6H | NMe$_2$ |
| 7.25 | ~5H | phenyl |

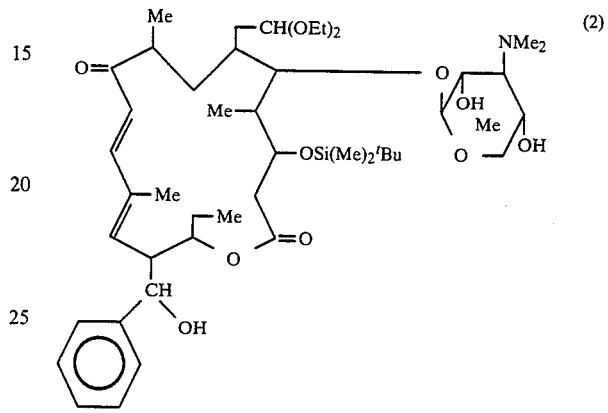
(2)

A solution of 432 mg of 2',4'-di-O-acetyl-3-O-tert-butyldimethylsilyl-23-C-phenylmycaminosyl tylonolide diethylacetal in 8.65 ml of methanol was kept at 50° C. overnight. Usual work-up gave 137 mg of 3-O-tert-butyldimethylsilyl-23-C-phenylmycaminosyl tylonolide diethylacetal.

| NMR (CDCl$_3$) | | |
|---|---|---|
| δ(ppm) | | |
| 0.93 | 9H | 3-O—Si(Me)$_2$$^t$Bu |
| 2.50 | 6H | NMe$_2$ |
| 4.37 | 1H | H—1' |
| 7.25 | 5H | phenyl |

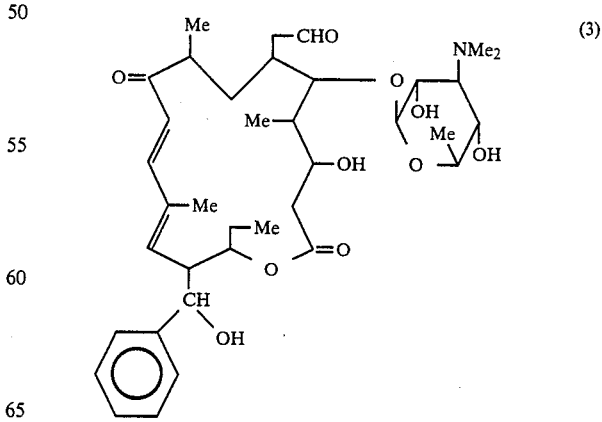
(3)

A solution of 137 mg of 3-O-tert-butyldimethylsilyl-23-C-phenylmycaminosyl tylonolide diethylacetal in 0.69 ml of acetonitrile and 0.69 ml of 1N hydrochloric acid was kept at room temperature overnight. Usual work-up as described in Ex. 1(3) gave, after chromatography (Kiesel gel-60: 13 g; chloroform:methanol: 28% aqueous ammonia: 15:1:0.1-12:1:0.1), 65.5 mg of 23-C-phenylmycaminosyl tylonolide.

| NMR (CDCl₃) | | |
|---|---|---|
| δ(ppm) | | |
| 2.50 | 6H | NMe₂ |
| 4.32 | 1H | H—1' |
| 5.47 | 1H | H—13 |
| 7.25 | 5H | phenyl |
| 9.74 | 1H | CHO |

EXAMPLE 8

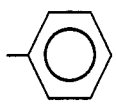

(1)

To a cold (−78° C.) solution 782 mg of 2',4'-di-O-acetyl-3-O-tert-butyl-dimethyl-23-deoxy-23-oxo silyl mycaminosyl tylonolide diethylacetal in 10 ml of tetrahydrofuran was added 2.5 ml of 1M ether solution of allyl magnesium bromide. After usual work-up as described in Ex.1(1) gave, after chromatography (toluene:ethyl acetate: 2:1 as eluant), 201 mg of one optical isomer (A) and 119 mg of another optical isomer (B) of 2',4'-di-O-acetyl-3-O-tert-butyldimethylsilyl-23-C-(2-propenyl)mycaminosyl tylonolide diethylacetal.

| NMR (CDCl₃) | | |
|---|---|---|
| (A) δ (ppm) | | |
| 0.90 | 9H | Si—tBu |
| 2.10 | 6H | 2.'4'-OCOMe |
| 2.40 | 6H | NMe₂ |
| 4.41 | 1H | H-1' |
| (B) δ (ppm) | | |
| 0.90 | 9H | Si—tBu |
| 2.10 | 6H | 2.'4'-OCOMe |
| 2.40 | 6H | NMe₂ |
| 6.32 | 1H | H-10 |

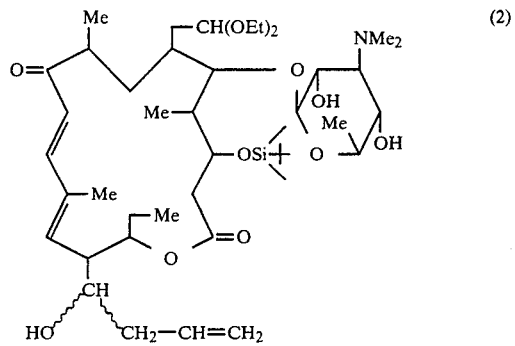

(2)

201 mg of the optical isomer (A) and 119 mg of the optical isomer (B) obtained at (1) above of 2',4'-di-O-acetyl-3-O-tert-butyl-dimethylsilyl-23-C-(2-propenyl)-mycaminosyl tylonolide diethylacetal were subjected to methanolysis respectively to give, after chromatography (chloroform:methanol: 28% aqueous ammonia: 30:1:0.1), 66 mg of one optical isomer (C) or 60 mg of another optical isomer (D) of 3-O-tert-butyldimethylsilyl-23-C-(2-propenyl)mycaminosyl tylonolide diethyl acetal as solid material.

| NMR (CDCl₃) | | |
|---|---|---|
| (C) δ (ppm) | | |
| 0.90 | 9H | Si—tBu |
| 1.86 | 3H | 22-Me |
| 2.55 | 6H | NMe₂ |
| 4.33 | 1H | H-1' |
| 6.27 | 1H | H-10 |
| (D) δ (ppm) | | |
| 0.90 | 9H | Si—tBu |
| 1.83 | 3H | 22-Me |
| 2.57 | 6H | NMe₂ |
| 4.33 | 1H | H-1' |
| 6.10 | 1H | H-13 |

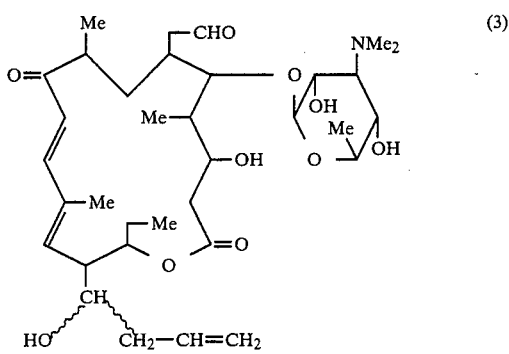

(3)

66 mg of the optical isomer (C) and 60 mg of the optical isomer (D) of 3-O-tert-butyldimethylsilyl-23-C-(2-propenyl)mycaminosyl tylonolide diethylacetal were hydrolyzed respectively. Usual manner gave, after chromatography (chloroform:methanol: 28% aqueous ammonia: 20:1:0.1), 40 mg of one optical isomer (E) or 39 mg of another optical isomer (F) of 23-C-(2-propenyl)mycaminosyl tylonolide as solid material.

| NMR (CDCl₃) | | |
|---|---|---|
| (E) δ (ppm) | | |
| 1.79 | 3H | 22-Me |

-continued

| NMR (CDCl₃) | | |
|---|---|---|
| 2.50 | 6H | NMe₂ |
| 4.27 | 1H | H-1' |
| 5.04~5.18 | 2H | H-26a.b. |
| 5.65~5.82 | 1H | H-25 |
| 6.11 | 1H | H-13 |
| 6.30 | 1H | H-10 |
| 7.40 | 1H | H-11 |
| 9.69 | 1H | H-20 |
| (F) δ (ppm) | | |
| 1.83 | 3H | 22-Me |
| 2.51 | 6H | NMe₂ |
| 4.29 | 1H | H-1' |
| 4.98 | 1H | H-15 |
| 5.13~5.23 | 2H | H-26a.b |
| 5.65~5.87 | 2H | H-13  H-25 |
| 6.25 | 1H | H-10 |
| 7.26 | 1H | H-11 |
| 9.70 | 1H | H-20 |

EXAMPLE 9

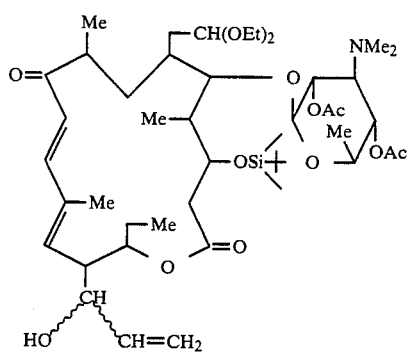
(1)

To a cold (−78° C.) solution of 903 mg of 2',4'-di-O-acetyl-3-O-tert-butyl-dimethylsilyl-23-deoxy-23-oxo-mycaminosyl tylonolide diethylacetal, was added vinyl magnesium bromide (2M tetrahydrofuran solution), and usual work-up gave, after to chromatography, 422 mg of one optical isomer (A) and 166 mg of another optical isomer (B) of 2',4'-di-O-acetyl-3-O-tert-butyldimethylsilyl-23-C-vinylmycaminosyl tylonolide diethylacetal respectively as solid material.

| NMR (CDCl₃) | | |
|---|---|---|
| (A) δ (ppm) | | |
| 0.91 | 9H | Si—tBu |
| 2.11 | 6H | 2.'4'-OCOMe |
| 2.40 | 6H | NMe₂ |
| 4.42 | 1H | H-1' |
| 6.30 | 1H | H-10 |
| (B) δ (ppm) | | |
| 0.90 | 9H | Si—tBu |
| 2.10 | 6H | 2.'4'-OCOMe |
| 2.40 | 6H | NMe₂ |
| 6.31 | 1H | H-10 |

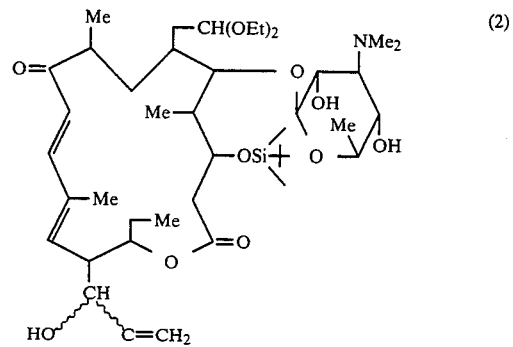
(2)

422 mg of the isomer (A) or 166 mg of the isomer (B) of 2,4-di-O-acetyl-3-O-tert-butyl dimethylsilyl-23-C-vinylmycaminosyl tylonolide diethylacetal was treated in similar manner for Example 8 (2) to give 350 mg of one isomer (C) or 73 mg of another isomer (D) of 3-O-tert-butyldimethylsilyl-23-C-vinylmycaminosyl tylonolide diethylacetal respectively as solid material.

| NMR (CDCl₃) | | |
|---|---|---|
| (C) (CDCl₃) | | |
| 0.87 | 9H | Si—tBu |
| 2.53 | 6H | NMe₂ |
| 4.30 | 1H | H-1' |
| 6.28 | 1H | H-10 |
| (D) δ (ppm) | | |
| 0.90 | 9H | Si-tBu |
| 2.55 | 6H | NMe₂ |
| 6.30 | 1H | H-10 |
| 7.25 | 1H | H-11 |

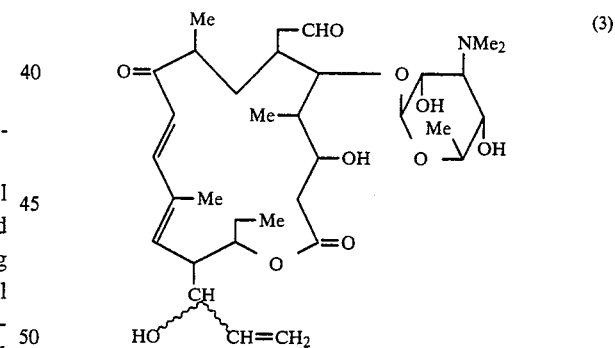
(3)

350 mg of the isomer (C) or 73 mg of the isomer (D) of 3-O-tert-butyldimethylsilyl-23-C-vinylmycaminosyl tylonolide diethylacetal was treated in simmilar manner for Example 8 (3) to give 186 mg of one isomer (E) or 45 mg of another isomer (F) of 23-C-vinylmycaminosyl tylonolide respectively as solid material.

| NMR (CDCl₃) | | | |
|---|---|---|---|
| (E) δ (ppm) | | | |
| 1.78 | 3H | 22-Me | |
| 2.52 | 6H | NMe₂ | |
| 4.28 | 1H | H-1' | |
| 4.39 | 1H | H-23 | |
| 5.14 | 1H | H-25a | |
| 5.2~5.3 | 2H | H-15 | H-25 b |
| 5.77 | 1H | H-24 | |
| 6.05 | 1H | H-13 | |
| 6.27 | 1H | H-10 | |

| NMR (CDCl₃) | | |
|---|---|---|
| 7.35 | 1H | H-11 |
| 9.59 | 1H | H-20 |
| (F) δ (ppm) | | |
| 1.84 | 3H | 22-Me |
| 2.51 | 6H | NMe₂ |
| 4.25~4.34 | 2H | H-1'  H-23 |
| 4.92 | 1H | H-15 |
| 5.27~5.36 | 2H | H-25a. b |
| 5.76 | 1H | H-13 |
| 5.92 | 1H | H-24 |
| 6.27 | 1H | H-10 |
| 7.29 | 1H | H-11 |
| 9.70 | 1H | H-20 |

EXAMPLE 10

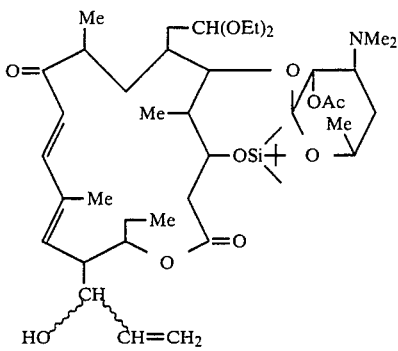
(1)

703 mg of 2'-O-acetyl-3-O-tert-butyldimethylsilyl-4'-deoxymycaminosyl tylonolide diethylacetal was treated in similar manner for Example 9 (1) to give 300 mg of one isomer (A) and 105 mg of another isomer (B) of 2'-O-acetyl-3-O-tert-butyldimethylsilyl-4'-deoxy-23-C-vinylmycaminosyl tylonolide diethylacetal respectively as solid material.

| NMR (CECl₃) | | |
|---|---|---|
| (A) δ (ppm) | | |
| 0.88 | 9H | Si—tBu |
| 2.11 | 3H | 2'-OCOMe |
| 2.30 | 6H | NMe₂ |
| 6.00 | 1H | H-13 |
| 6.29 | 1H | H-10 |
| (B) δ (ppm) | | |
| 0.88 | 9H | Si—tBu |
| 2.10 | 3H | 2'-OCOMe |
| 2.29 | 6H | NMe₂ |
| 5.71 | 1H | H-13 |
| 6.27 | 1H | H-10 |

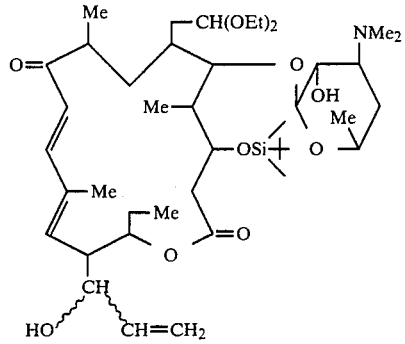
(2)

300 mg of the isomer (A) or 105 mg of the isomer (B) of 2'-O-acetyl-3-O-tert-butyldimethylsilyl-4'-deoxy-23-C-vinylmycaminosyl tylonolide diethylacetal was treated in simmilar manner for example 8 (2) to give 175 mg of one optical isomer (C) or 65 mg of another optical isomer (D) of 3-O-tert-butyldimethylsilyl-4'-deoxy-23-C-vinylmycaminosyl tylonolide diethylacetal respectively as solid material.

| NMR (CDCl₃) | | |
|---|---|---|
| (C) δ (ppm) | | |
| 0.90 | 9H | Si—tBu |
| 2.33 | 6H | NMe₂ |
| 4.77 | 1H | H-20 |
| 6.30 | 1H | H-10 |
| (D) δ (ppm) | | |
| 0.91 | 9H | Si—tBu |
| 2.32 | 6H | NMe₂ |
| 6.31 | 1H | H-10 |
| 7.27 | 1H | H-11 |

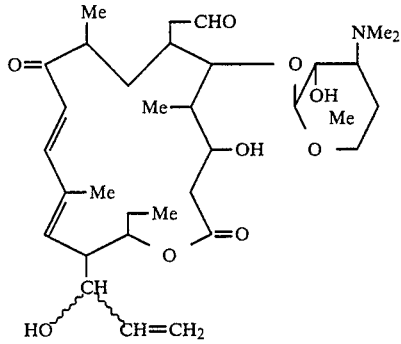
(3)

175 mg of the isomer (C) or 65 mg of the isomer (D) of 3-O-tert-butyldimethylsilyl-4'-deoxy-23-C-vinylmycaminosyl tylonolide diethylacetal was treated in simmilar manner for Example 8 (3) to give 86 mg of one isomer (E) and 41 mg of another isomer (F) of 4'-deoxy-23-C-vinylmycaminosyl tylonolide respectively as solid material.

| NMR (CDCl₃) | | |
|---|---|---|
| (E) δ (ppm) | | |
| 1.76 | 3H | 22-Me |
| 2.27 | 6H | NMe₂ |
| 4.22 | 1H | H-1' |
| 4.41 | 1H | H-23 |
| 5.1~5.3 | 3H | H-25a,b, H-15 |
| 5.77 | 1H | H-24 |

| NMR (CDCl₃) | | |
|---|---|---|
| -continued | | |
| 6.09 | 1H | H-13 |
| 6.30 | 1H | H-10 |
| 9.70 | 1H | H-20 |
| (F) δ (ppm) | | |
| 1.82 | 3H | 22-Me |
| 2.27 | 6H | NMe₂ |
| 4.23 | 1H | H-1' |
| 4.34 | 1H | H-23 |
| 4.91 | 1H | H-15 |
| 5.28~5.38 | 2H | H-25a,b |
| 5.79 | 1H | H-13 |
| 5.94 | 1H | H-24 |
| 6.31 | 1H | H-10 |
| 7.31 | 1H | H-11 |
| 9.71 | 1H | H-20 |

EXAMPLE 11

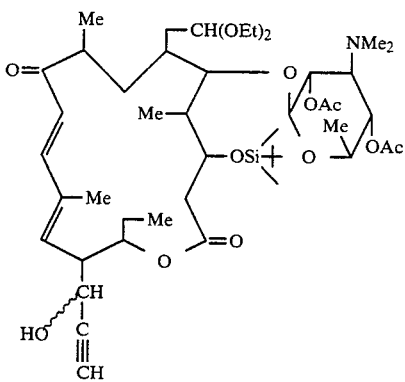
(1)

832 mg of 2',4'-di-O-acetyl-3-O-tert-butyldimethylsilyl-23-deoxy-23-oxo-mycaminosyl tylonolide diethylacetal was treated with ethynyl magnesium bromide (tetrahydrofuran solution) to give 160 mg of one isomer (A) and 177 mg of another isomer (B) of 2',4'-di-O-acetyl-3-O-tert-butyldimethylsilyl-23-C-ethynylmycaminosyl tylonolide diethylacetal respectively as solid material.

| NMR (CDCl₃) | | |
|---|---|---|
| (A) δ (ppm) | | |
| 0.90 | 9H | Si—tBu |
| 2.10 | 6H | 2',4'-OCOMe |
| 2.41 | 6H | NMe₂ |
| 6.08 | 1H | H-13 |
| 6.33 | 1H | H-10 |
| (B) δ (ppm) | | |
| 0.90 | 9H | Si—tBu |
| 2.10 | 6H | 2',4'-OCOMe |
| 2.40 | 6H | NMe₂ |
| 6.10 | 1H | H-13 |
| 6.30 | 1H | H-10 |

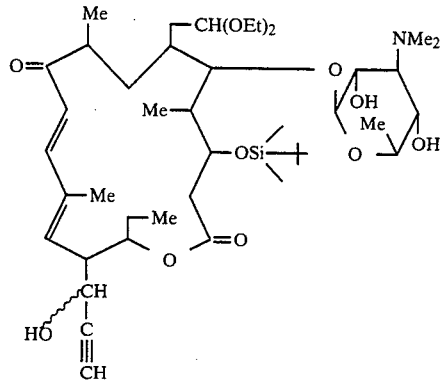
(2)

160 mg of the isomer (A) or 177 mg of the isomer (B) of 2',4'-di-O-acetyl-3-O-tert-butyldimethylsilyl-23-C-ethylmycaminosyl tylonolide diethylacetal was treated in simmilar manner for Example 8 (2) to give 109 mg of one isomer (C) or 129 mg of another isomer (D) of 3-O-tert-butyldimethylsilyl-23-C-ethynylmycaminosyl tylonolide diethylacetal respectively as solid material.

| NMR (CDCl₃) | | |
|---|---|---|
| (C) δ (ppm) | | |
| 0.88 | 9H | Si—tBu |
| 2.53 | 6H | NMe₂ |
| 4.30 | 1H | H-1' |
| 6.05 | 1H | H-13 |
| 6.32 | 1H | H-10 |
| 7.30 | 1H | H-11 |
| (D) δ (ppm) | | |
| 0.88 | 9H | Si—tBu |
| 2.55 | 6H | NMe₂ |
| 4.33 | 1H | H-1' |
| 5.10 | 1H | H-15 |
| 6.15 | 1H | H-13 |
| 6.30 | 1H | H-10 |

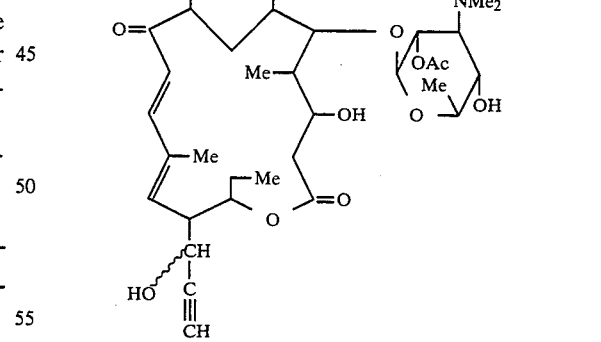
(3)

109 mg of the isomer (C) or 129 mg of the isomer (D) of 3-O-tert-butyldimethylsilyl-23-C-ethynylmycaminosyl tylonolide diethylacetal was treated in simmilar manner for Example 8 (3) to give 75.5 mg of one isomer (E) or 101 mg of another isomer (F) of 23-C-ethinyl-mycaminosyl tylonolide respectively as solid material.

| NMR (CDCl₃) | | |
|---|---|---|
| (E) δ (ppm) | | |
| 1.84 | 3H | 22-Me |
| 2.51 | 6H | NMe₂ |

| NMR (CDCl₃) | | |
|---|---|---|
| 4.28 | 1H | H-1' |
| 4.63 | 1H | H-23 |
| 5.23 | 1H | H-15 |
| 6.12 | 1H | H-13 |
| 6.34 | 1H | H-10 |
| 7.39 | 1H | H-11 |
| 9.70 | 1H | H-20 |
| (F) δ (ppm) | | |
| 1.85 | 3H | 22-Me |
| 2.51 | 6H | NMe₂ |
| 2.74 | 1H | H-25 |
| 4.27 | 1H | H-1' |
| 4.58 | 1H | H-23 |
| 5.10 | 1H | H-15 |
| 6.12 | 1H | H-13 |
| 6.30 | 1H | H-10 |
| 7.43 | 1H | H-11 |
| 9.69 | 2H | H-20 |

EXAMPLE 12

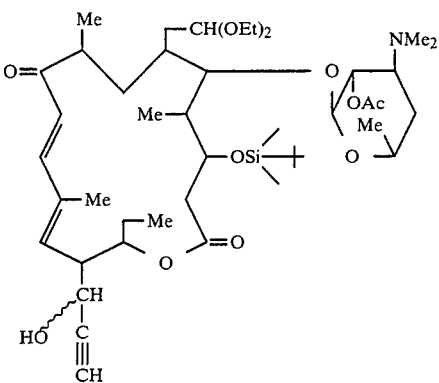
(1)

814 mg of 2'-O-acetyl-3-O-tert-butyldimethylsilyl-4'-deoxymycaminosyltylonolide diethylacetal was treated in similar manner for Example 11 (1) to give 103 mg of one isomer (A) and 118 mg of another isomer (B) of 2'-O-acetyl-3-O-tert-butyldimethyl-4'-deoxy-23-C-ethynylmycaminosyl tylonolide diethylacetal respectively as solid material.

| NMR (CDCl₃) | | |
|---|---|---|
| (A) δ (ppm) | | |
| 0.90 | 9H | Si—tBu |
| 2.12 | 3H | 2'-OCOMe |
| 2.30 | 6H | NMe₂ |
| 6.07 | 1H | H-13 |
| 6.33 | 1H | H-10 |
| (B) δ (ppm) | | |
| 0.89 | 9H | Si—tBu |
| 2.10 | 3H | 2'-OCOMe |
| 2.30 | 6H | NMe₂ |
| 6.03 | 1H | H-13 |
| 6.30 | 1H | H-10 |

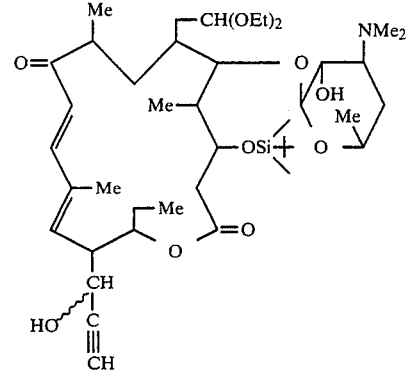
(2)

103 mg of the isomer (A) or 118 mg of the isomer (B) of 2'-O-acetyl-3-O-tert-butyldimethylsilyl-4'-deoxy-23-C-ethynylmycaminosyl tylonolide diethylacetal was treated in similar manner to Example 8 (2) to give 62 mg of one isomer (C) or 70 mg of another isomer (D) of 3-O-tert-butyldiemthylsilyl-4'-deoxy-23-C-ethynylmycaminosyl tylonolide diethylacetal respectively as solid material.

| NMR (CDCl₃) | | |
|---|---|---|
| (C) δ (ppm) | | |
| 0.88 | 9H | Si—tBu |
| 2.31 | 6H | NMe₂ |
| 5.28 | 1H | H-15 |
| 6.07 | 1H | H-13 |
| 6.33 | 1H | H-10 |
| (D) δ (ppm) | | |
| 0.87 | 9H | Si—tBu |
| 2.30 | 6H | NMe₂ |
| 5.03 | 1H | H-15 |
| 6.07 | 1H | H-13 |
| 6.30 | 1H | H-10 |

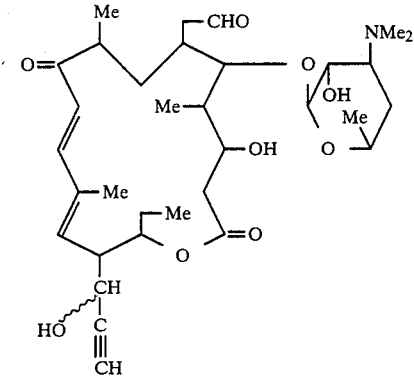
(3)

62 mg of the isomer (C) or 70 mg of the isomer (D) of 3-O-tert-butyldimethylsilyl-4'-deoxy-23-C-ethynylmycaminosyl tylonolide diethylacetal was treated in similar manner to Example 8 (3) to give 38 mg of one isomer (E) or 40 mg of another isomer (F) of 4'-deoxy-23-C-ethynylmycaminosyl tylonolide respectively as solid material.

| NMR (CDCl₃) | | |
|---|---|---|
| (E) δ (ppm) | | |
| 1.82 | 3H | 22-Me |

| -continued | | |
|---|---|---|
| NMR (CDCl$_3$) | | |
| 2.27 | 6H | NMe$_2$ |
| 2.50 | 1H | H-25 |
| 4.23 | 1H | H-1' |
| 4.64 | 1H | H-23 |
| 5.23 | 1H | H-15 |
| 6.13 | 1H | H-13 |
| 6.34 | 1H | H-10 |
| 7.42 | 1H | H-11 |
| 9.72 | 1H | H-20 |
| (F) δ (ppm) | | |
| 1.84 | 3H | 22-Me$_2$ |
| 2.28 | 6H | NMe$_2$ |
| 2.70 | 1H | H-25 |
| 4.22 | 1H | H-1' |
| 4.57 | 1H | H-23 |
| 5.08 | 1H | H-15 |
| 6.11 | 1H | H-13 |
| 6.35 | 1H | H-10 |
| 7.43 | 1H | H-11 |
| 9.72 | 1H | H-20 |

What is claimed is:

1. A 23-C-substituted mycaminosyl tylonolide compound of the following formula:

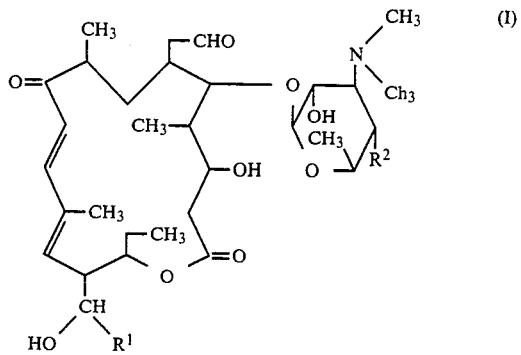

wherein R$^1$ represents lower alkyl, aryl, lower alkenyl or lower alkynyl, R$^2$ represents hydrogen or hydroxyl.

2. A compound according to claim 1, wherein R$^1$ represents lower alkyl, lower alkenyl, or lower alkynyl.

3. A pharmaceutical composition containing an effective amount of a compound of claim 1 and a pharmaceutically acceptable non-toxic carrier.

4. A method of producing an antibacterial activity against bacteria by administering a compound of claim 1 to a host in need of such treatment.

5. The mycaminosyl tylonolide compound of claim 1, wherein R$^1$ is methyl and R$^2$ is hydroxyl.

6. The mycaminosyl tylonolide compound of claim 1, wherein R$^1$ is ethyl and R$^2$ is hydroxyl.

7. The mycaminosyl tylonolide compound of claim 1, wherein R$^1$ is methyl and R$^2$ is hydrogen.

8. The mycaminosyl tylonolide compound of claim 1, wherein R$^1$ is phenyl and R$^2$ is hydroxyl.

9. The mycaminosyl tylonolide compound of claim 1, wherein R$^1$ is propyl and R$^2$ is hydroxyl.

10. The mycaminosyl tylonolide compound of claim 1, wherein R$^1$ is vinyl and R$^2$ is hydroxyl.

11. The mycaminosyl tylonolide compound of claim 1, wherein R$^1$ is vinyl and R$^2$ is hydrogen.

12. The mycaminosyl tylonolide compound of claim 1, wherein R$^1$ is ethynyl and R$^2$ is hydroxyl.

13. The mycaminosyl tylonolide compound of claim 1, wherein R$^1$ is ethynyl and R$^2$ is hydrogen.

* * * * *